United States Patent [19]

Gscheidmeier et al.

[11] 4,081,425

[45] Mar. 28, 1978

[54] PROCESS FOR THE MANUFACTURE OF LIGHT COLOR TERPENEPHENOLS

[75] Inventors: Manfred Gscheidmeier, Gablingen; Karl Hacker, Augsburg, both of Germany

[73] Assignee: Hoechst Aktiengesellschaft, Frankfurt am Main, Germany

[21] Appl. No.: 775,837

[22] Filed: Mar. 9, 1977

Related U.S. Application Data

[63] Continuation-in-part of Ser. No. 742,209, Nov. 16, 1976, abandoned.

[30] Foreign Application Priority Data

Nov. 21, 1975 Germany .............................. 2552175

[51] Int. Cl.$^2$ ............................................. C08G 61/00
[52] U.S. Cl. ...................................................... 260/62
[58] Field of Search ..................................... 260/62, 51

[56] References Cited

U.S. PATENT DOCUMENTS

| 2,466,889 | 4/1949 | Geiger ..................................... 260/62 |
| 2,471,453 | 5/1949 | Rummelsburg ........................ 260/62 |
| 2,471,455 | 5/1949 | Rummelsburg ........................ 260/62 |
| 2,596,235 | 5/1952 | Geiger ............................... 260/51 R |
| 3,953,402 | 4/1976 | Kline ...................................... 260/62 |

Primary Examiner—Ronald W. Griffin
Attorney, Agent, or Firm—Connolly and Hutz

[57] ABSTRACT

Process for the manufacture of light color terpenephenols by reaction of terpene hydrocarbons with phenols in the presence of a heavily acidic cation exchange resin or a bleaching earth and in the presence of phenol condensation products.

2 Claims, No Drawings

PROCESS FOR THE MANUFACTURE OF LIGHT COLOR TERPENEPHENOLS

This is a continuation-in-part of copending application Ser. No. 742,209, filed Nov. 16, 1976, now abandoned.

It is known that terpene hydrocarbons or terpene derivatives giving terpene hydrocarbons under corresponding reaction conditions may be reacted with phenols in the presence of catalysts such as strong acids, Lewis acids or bleaching earths to yield more or less pure terpenephenols. In a first reaction step, terpenephenol ethers are formed which rearrange in a second reaction step to give the terpenephenols.

In the literature, numerous preparation methods for terpenephenols are described. According to German Patent No. 598,298, for example, olefins or cyclic alkylenes are reacted with phenols or the derivatives thereof in the presence of surface catalysts such as finely distributed bleaching earths, at temperatures of from 100° to 200° C and under elevated pressure. By vacuum distillation at very high temperatures, the terpenephenols formed are subsequently separated from the catalysts which cannot be reused. According to German Patent No. 743,863, the reaction is carried out also at temperatures below 100° C when metal halides such as AlCl$_3$, ZnCl$_2$, FeCl$_3$ are employed as catalysts. The reaction products are distilled off by means of steam in order to liberate them from excess reactants before separating the product with considerable expenditure from the catalysts which have to be used in a relatively high concentration. Swiss Patent No. 295,065 discloses the reaction to be carried out in the presence of boron trifluoride or molecule compounds thereof at a temperature of from 70° to 100° C. Subsequently, the boron trifluoride is hydrolyzed, and then the hydrofluoric and boric acid which have formed are eliminated by steam distillation together with unreacted starting substances. Similar operations are described in U.S. Pat. No. 2,471,455; however, in this case the reaction is carried out with addition of a solvent, for example benzene, and at temperatures of from 10° to 30° C. In a paper of W. Minematu and Y. Matsubara, Nippon Kagaku Kaishi 12, 2361, (1974), which deals with comparative tests about the reaction of camphene with o-cresol, also cationic exchange resins are cited as suitable catalysts besides the known ones.

The decisive disadvantage of all hitherto known processes for the manufacture of terpenephenols resides in the fact that the final products have a more or less brown color due to their content of dark colored oxidation or polymerization products. Since terpenephenols may also be used as execellent light stabilizers for security glass sheetings, they should of course have a color as light as possible. Therefore, expensive aftertreatments, for example vacuum distillation, catalytic hydrogenation etc., are required to follow the manufacturing process as such in order to brighten the products. Furthermore, it is disadvantageous that the reactions in the presence of Friedel-Crafts catalysts exclude a reuse of these latter catalysts, thus causing pollution problems for water and air.

It has now been found that terpenephenols of a very light color may be obtained in simple manner when the reaction is carried out in the presence of cation exchange resins or bleaching earths as catalysts and of antioxidants, and when the catalyst is eliminated before the work-up.

The present invention provides therefore a process for the manufacture of light color terpenephenols by reaction of terpene hydrocarbons with phenols in the presence of from 5 to 20% by weight (relative to the terpene hydrocarbon) of a cation exchange resin or a bleaching earth as catalyst, at a temperature of from 50° to 100° C, which comprises using a heavily acidic, completely anhydrous cation exchange resin or an anhydrous bleaching earth, operating in the presence of from 0.01 to 5.0% by weight (relative to the terpene hydrocarbon) of an antioxidant of the formulae I, II or III

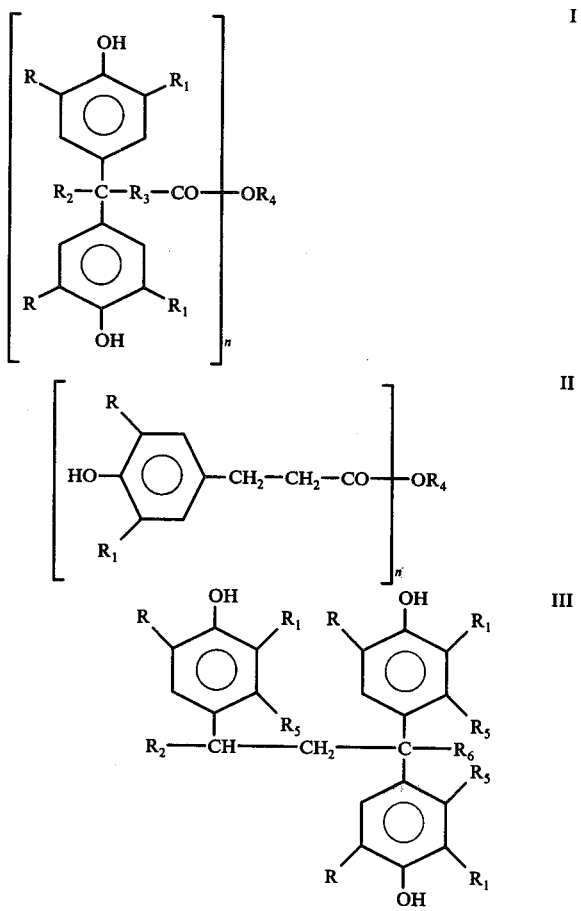

where
$n$ is 1, 2, 3 or 4
R is alkyl having from 1 to 4 carbon atoms,
R$_1$, R$_2$ and R$_5$ each are H or alkyl having from 1 to 4 carbon atoms,
R$_3$ is alkylene having from 1 to 6 carbon atoms,
R$_4$ is mono-, di-, tri- or tetrahydric alcohol having from 1 to 30 carbon atoms, and
R$_6$ is H or alkyl having from 1 to 6 carbon atoms, separating the catalyst from the reaction mixture after the reaction is complete, and subsequently blowing off unreacted starting substances by means of steam.

The terpenephenols obtained in accordance with this invention are resinous and nearly colorless, and they do not require any after-treatment. When they are formed on the basis of camphene, they have an iodine color number of 1 to 2 in a 50% solution in toluene, while solutions having the same concentration of product prepared according to known methods have an iodine color number of 15 to 20 (before a possibly necessary after-treatment). Terpenephenols from other terpenes, for example alpha-pinene or Δ-3-carene, which have a black color when manufactured according to known methods, are obtained according to the present invention with an iodine color number (in toluene) of from 3 to 5. The viscosity of the resins at 60° C is superior to 2000 cP, and about 4 cP at 20° C as a 50% solution in toluene. A further advantage of the operation mode of the invention resides in the fact that the exchange resins or bleaching earths serving as catalysts can be reused, optionally after previous regeneration.

The terpenephenols are obtained by reaction of terpene hydrocarbons with phenols. If necessary, a solvent inert under the reaction conditions, for example toluene, may be present.

Suitable terpene hydrocarbons are preferably bicyclic monoterpenes such as camphene, fenchene, Δ-3-carene or alpha-pinene, furthermore monocyclic monoterpenes having at least one double bond such as dipentene, and tricyclic monoterpenes such as tricyclene or cyclofenchene. Mixtures of terpene hydrocarbons may of course also be used.

As phenol component, there may be used for example: unsubstituted phenol, and preferably monophenols having from 1 to 3 alkyl substituents containing from 1 to 12 carbon atoms, preferably methyl or ethyl groups, one carbon atom at least however being unsubstituted in o- or p-position to the OH group. Preferred examples are the cresols and dimethyl-phenols, of the latter ones especially 3,4-dimethylphenol [= 1,2-xylenol (4)], furthermore tert.-butylphenols, butylphenols and dodecylphenols. Optionally, also arylsubstituted phenols and naphthols may be used or mixtures of phenols, for example commercial industrial-grade cresol mixtures.

Suitable cation exchange resins are heavily acidic ion exchange resins of macroporous structure having a grain size of about 0.1 to 1.5 mm which must be strictly anhydrous, such as commercial resins generally on the basis of nucleo-sulfonated copolymers of styrene and divinylbenzene, for example AMBERLYST 15 of Rohm & Haas or LEWATIT SPC 108/H of Bayer AG. The safest method for rendering the exchange resin anhydrous is a pretreatment with acetic acid anhydride. In order to prevent damaging of the catalyst, however, it is recommended to operate with the use of from 95 to 50% by weight of acetic acid and from 5 to 50% by weight of acetic anhydride; a preliminary swelling in acetic acid being useful. Depending on the degree of dilution and the water content of the ion exchanger, a more or less exothermic reaction is observed during this operation. After separation of the acetic acid/anhydride mixture, the resin is after-treated either by vacuum drying or washing with an anhydrous organic solvent, for example toluene. This method is furthermore very suitable for regenerating the ion exchange resin after it has lost its activity. However, before the treatment with anhydride, it has to be thoroughly washed with an organic solvent, for example toluene, in order to clear the pores and to ensure a sufficient surface in the ion exchange resin.

By bleaching earths, also called fuller's earths, Florida earths or bentonites, there are to be understood most finely distributed commercial aluminum/magnesium silicates from the montmorillonite group. A suitable product is Catalyst KSF of Messrs. Sudchemie, Munich. Also the bleaching earth has to be anhydrous.

The amount of catalyst is from 5 to 20, preferably 10 to 15, % by weight relative to the terpene hydrocarbon.

Suitable antioxidants used in the reaction in amounts of from 0.01 to 5, preferably from 0.1 to 3, and especially from 0.2 to 1, % by weight relative to the terpene hydrocarbon, are mono- or polynuclear phenol condensation products having the following structures

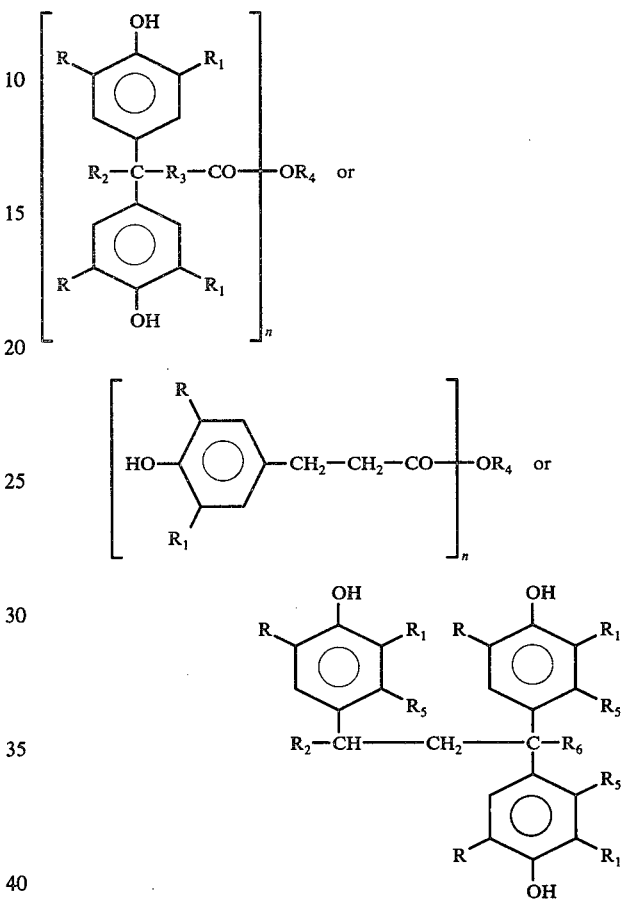

where
$n$ is 1, 2, 3 or 4,
$R$ is alkyl having from 1 to 4 carbon atoms, preferably tert.-butyl,
$R_1$ is H or alkyl having from 1 to 4 carbon atoms, preferably H or tert.-butyl,
$R_2$ is H, alkyl having from 1 to 4 carbon atoms, preferably $CH_3$,
$R_3$ is alkylene having from 1 to 6 carbon atoms, preferably $—CH_2—$,
$R_4$ is mono- to tetrahydric alcohol having from 1 to 30 carbon atoms, preferably derived from stearyl alcohol, ethyleneglycol or pentaerythritol,
$R_5$ is H, alkyl having from 1 to 4 carbon atoms, preferably $CH_3$, and
$R_6$ is H or alkyl having from 1 to 6 carbon atoms, preferably H.

Suitable compounds are for exchange 3,5-di-tert.-butyl-4-hydroxyphenyl-propanoic acid pentaerythritol ester or -stearyl ester, 1,1,3-tris-(2'-methyl-4'-hydroxy-5'-tert.butylphenyl)-butane and di-[3,3-bis-(4-hydroxy-3-tert.-butylphenyl)-butanoic acid] glycol ester; the latter compound being especially recommended. Before the start of the reaction, the antioxidant is added to one of the two reactants, especially the phenolic one If the radicals of the structures

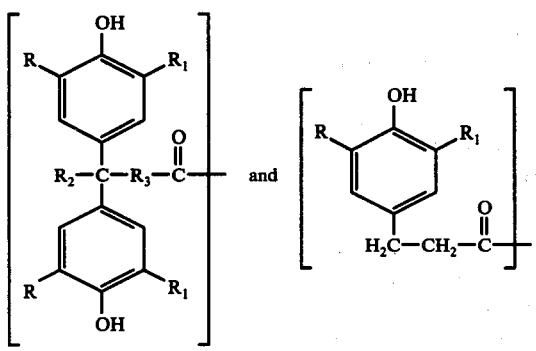

are symbolized by X and Y, respectively, the claimed antioxidants of formula I and II can be symbolized as

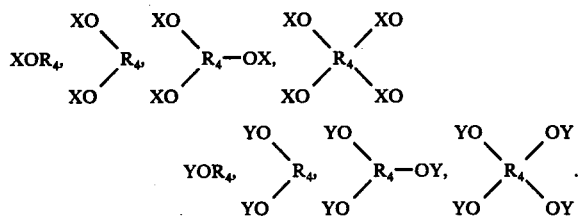

The compounds

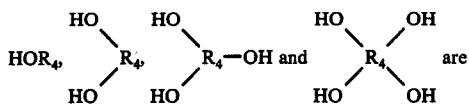

the corresponding mono-, di-, tri- and tetra-hydric alcohols, respectively, from which the claimed ester-antioxidants are derived. Said alcohols have 1 to 30 carbon atoms if they are monohydric, 2 to 30 carbon atoms if they are dihydric, 3 to 30 carbon atoms if they are trihydric, and 4 to 30 carbon atoms if they are tetrahydric. The said minimum numbers 1, 2, 3, 4, respectively, of the carbon atoms follow of course from the fact, that no stable alcohols exist which carry more than one hydroxy group at any carbon atom. Each of the hydroxy groups of the mono-, di-, tri-, tetra-hydric alcohols shall be esterified by an X or Y radical.

In order to obtain the intended light color terpenephenol resins, not only the above measures for the reaction have to be taken, but also the kind of work-up of the reaction mixtures is of considerable importance. While according to the known processes the catalysts or their decomposition products remain in the reaction mixture during the final steam treatment for the elimination of unreacted starting material (or are removed only later on), it is an essential characteristic of the process of the invention that the catalyst is removed before the batches are worked up. Because of the solid, large-grain structure of the catalyst, this removal, for example by sedimentation of filtration, is not at all difficult. The reaction mixtures liberated from the catalyst are subsequently worked up in known manner, thus yielding the light color resins having the cited color numbers.

It is advantageous to carry out the process of the invention on a large scale in a semi-continuous manner in a cycle system when exchange resins are used as catalyst; that is, one reaction tower (a column containing loosely charged ion exchange resins in stationary arrangement) and a buffer vessel are coupled in a cycle with a pump. After complete reaction, the product is liberated from unreacted components by steam distillation in the buffer vessel. If necessary, the ion exchange resin may be regenerated without removing it from the reaction tower.

When bleaching earths are used as catalyst, it is advantageous to operate in vessels with agitator and to separate the catalyst by filtration before the steam treatment of the reaction mixture.

The light color terpenephenol resins obtained according to the operation mode of the invention are suitable for example as additives for oil lacquers, printing inks, dry-bright polishes, adhesive tapes or record manufacturing compositions, and as stabilizers preferably in fields requiring a light color, as for example the manufacture of sheetings for security glass.

The following examples illustrate the invention and show the color improvement as compared to products obtained according to known processes.

EXAMPLE 1

In a round-bottom flask with agitator having a capacity of 1 liter, 200 g of xylenol (3,4-dimethylphenol) are molten at 60°-70° C under a nitrogen blanket with addition of 0.3 g of di-[3,3-bis(4-hydroxy-3-tert.-butylphenyl)-butanoic acid]-glycol ester. Subsequently, 30 g of a heavily acidic cation exchange resin (LEWATIT SPC 108/H of Bayer AG), which has been treated previously with 100 ml of a mixture of 70% by weight of acetic acid and 30% by weight of acetic anhydride and then washed with anhydrous toluene are added, and at an inner temperature of 70°-75° C, 223 g of industrial-grade camphene (which may contain up to 25% by weight of tricyclene) are fed in slowly and with agitation in such a manner that the temperature does not exceed 75° C. Subsequently, the agitation is continued at 70° C for a further 20 hours. After having switched off the agitator, the catalyst is allowed to settle and the reaction product is carefully poured into another flask, where steam is blown through it until no xylenol can be detected any more in the condensate. The resulting product is dried at 70° C with reduced pressure, and it solidifies on cooling to form a viscous, nearly colorless resin. The iodine color number of a 50% solution in toluene is from 1 to 2, the OH number 5.6.

EXAMPLE 2

Operations are carried out under the conditions of Example 1; however, instead of the exchange resin, 40 g of an anhydrous bleaching earth (Catalyst KSF of Messrs. Sudchemie, Munich) are used as catalyst. The resin obtained has an iodine color number of 1 (50% solution in toluene) and an OH number of 5.9.

EXAMPLE 3

In the same manner as described in Example 1, a terpenephenol resin is prepared from 200 g of an industrial-grade cresol mixture (23% by weight of phenol, 23% by weight of o-cresol, 25% by weight of m-cresol, 12% by weight of p-cresol, remainder dimethylphenols) and 340 g of camphene. Iodine color number of the 50% solution in toluene: 1-2, OH number: 4.4.

EXAMPLE 4

In the manner as described in Example 1, 200 g of cresol mixture are reacted with 340 g of Δ-3-carene. A resin is obtained the 50% solution of which in toluene has an iodine color number of 4 and an OH number of 4.0.

EXAMPLE 5

In the manner as described in Example 1, 200 g of cresol mixture and 340 g of alpha-pinene are reacted, but at a maximum 85° C. A terpenephenol having the iodine color number 5 (50% solution in toluene) and an OH number of 4.2 is obtained.

EXAMPLES 6 to 8

Operations are as described in Example 1, however, each time 0.3 g of the following antioxidants are used:
a. 3,5-di-tert.-butyl-4-hydroxyphenyl-propanoic acid pentaerythritol ester
b. 3,5-di-tert.-butyl-4-hydroxyphenyl-propanoic acid stearyl ester
c. 1,1,3-tris-(2'-methyl-4'-hydroxy-5'-tert.-butylphenyl)-butane.

The terpenephenols obtained have the following characteristics:

| Antioxidant | Iodine color number**) | OH number |
|---|---|---|
| a | 2 | 5.2 |
| b | 1-2 | 5.2 |
| c | 1-2 | 5.3 |

*)50 T solution of the terpenephenol in toluene

COMPARATIVE EXAMPLE 1

This example proves that the reaction of xylenol with camphene according to the known process using boron fluoride as catalyst yields a considerably darker terpenephenol. Operations are as described in Example 1, however, there is no addition of antioxidant and exchange resin, only 7 g boron fluoride/glacial acetic acid are added. After the reaction is complete, the catalyst is hydrolyzed by adding about 20 ml of water, subsequently the excess amount of water is suction-filtered from the surface of the resin, and the letter one is then treated with steam as indicated and dried. A dark brown, viscous resin is obtained the 50% solution in toluene of which has an iodine color number of 15-20 and an OH number of 5.8.

COMPARATIVE EXAMPLE 2

Operations are also as described in Example 1, however, the antioxidant is omitted and the ion exchanger is separated only after the steam distillation. The 50% solution in toluene of the product obtained has an iodine color number of about 8 and an OH number of 5.6.

COMPARATIVE EXAMPLE 3

Operations are carried out as described in Example 1, that is, in the presence of exchange resin and antioxidant; however, the exchange resin is separated not before but after the steam treatment. The 50% solution in toluene of this terpenephenol has an iodine color number of 5 and an OH number of 5.6.

What is claimed is:

1. A process for the manufacture of light color terpenephenols by reaction of terpene hydrocarbons with phenols in the presence of from 5 to 20% by weight (relative to the terpene hydrocarbon) of a cation exchange resin or a bleaching earth as catalyst, at a temperature of from 50° to 100° C, which comprises using a heavily acidic, completely anhydrous cation exchange resin or an anhydrous bleaching earth, operating in the presence of from 0.01 to 5.0% by weight (relative to the terpene hydrocarbon) of an antioxidant of the formulae I, II or III

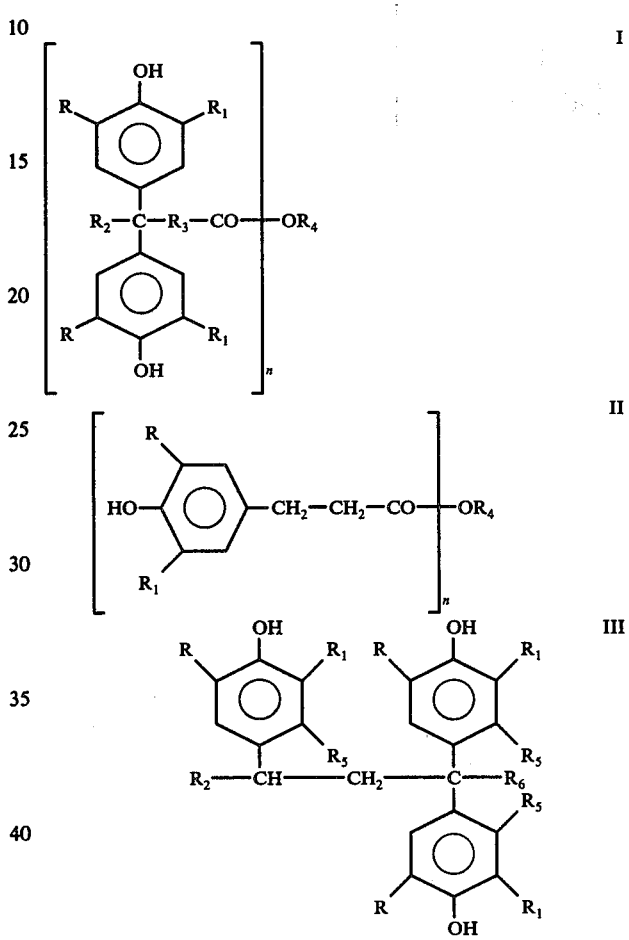

where
$n$ is 1, 2, 3 or 4,
R is alkyl having from 1 to 4 carbon atoms,
$R_1$, $R_2$ and $R_5$ each are H or alkyl having from 1 to 4 carbon atoms,
$R_3$ is alkylene having from 1 to 6 carbon atoms,
$R_4$ is mono-, di-, tri- or tetrahydric alcohol having from 1 to 30 carbon atoms, and
$R_6$ is H or alkyl having from 1 to 6 carbon atoms, separating the catalyst from the reaction mixture after the reaction is complete, and subsequently blowing off unreacted starting substances by means of steam.

2. The process as claimed in claim 1, which comprises using from 0.1 to 3.0% by weight, relative to the terpene hydrocarbon, of di-[3,3-bis(4-hydroxy-3-tert.-butylphenyl)-butanoic acid]-glycol ester as antioxidant.

* * * * *